(12) United States Patent
Gilbert et al.

(10) Patent No.: US 7,041,257 B2
(45) Date of Patent: May 9, 2006

(54) MICROFABRICATED TWO-PIN LIQUID SAMPLE DISPENSING SYSTEM

(75) Inventors: John Gilbert, Brookline, MA (US); John Harley, Sausalito, CA (US)

(73) Assignee: Cytonome, Inc., Watertown, MA (US)

( * ) Notice: Subject to any disclaimer, the term of this patent is extended or adjusted under 35 U.S.C. 154(b) by 394 days.

(21) Appl. No.: 10/027,171

(22) Filed: Dec. 21, 2001

(65) Prior Publication Data

US 2003/0059345 A1    Mar. 27, 2003

Related U.S. Application Data

(60) Provisional application No. 60/325,001, filed on Sep. 25, 2001.

(51) Int. Cl.
*B01L 3/02* (2006.01)
*B01N 3/00* (2006.01)
*G01N 15/06* (2006.01)
*G01N 1/10* (2006.01)
*G01N 1/04* (2006.01)

(52) U.S. Cl. .................. 422/100; 422/68.1; 422/99; 436/180

(58) Field of Classification Search .......... 422/99–100, 422/68.1; 73/864.42; 436/180; 141/255; 294/99.2; 606/210; 222/420; 347/6–9, 347/19, 109
See application file for complete search history.

(56) References Cited

U.S. PATENT DOCUMENTS

| | | | |
|---|---|---|---|
| 3,885,440 A | 5/1975 | Rossfelder | 73/425.2 |
| 4,116,069 A | 9/1978 | Lezgintsev et al. | 73/425.2 |
| 4,659,677 A | 4/1987 | Glover et al. | 436/174 |
| 5,260,030 A | 11/1993 | DeVaughn | 422/100 |
| 5,356,052 A | 10/1994 | Poynter | |
| 5,722,989 A * | 3/1998 | Fitch et al. | 606/205 |
| 5,741,554 A | 4/1998 | Tisone | 427/424 |
| 5,770,151 A | 6/1998 | Roach et al. | 422/63 |
| 5,807,522 A | 9/1998 | Brown et al. | 422/50 |
| 5,957,167 A | 9/1999 | Feygin | 141/31 |
| 5,962,329 A | 10/1999 | Ershov et al. | 436/50 |
| 6,001,231 A | 12/1999 | Kopf-Sill | 204/454 |
| 6,024,925 A | 2/2000 | Little et al. | 422/100 |
| 6,086,825 A | 7/2000 | Sundberg et al. | 422/100 |
| 6,101,946 A | 8/2000 | Martinsky | 101/494 |
| 6,110,426 A | 8/2000 | Shalon et al. | 422/68.1 |
| 6,245,297 B1 | 6/2001 | Kowallis | 422/66 |
| 6,255,119 B1 | 7/2001 | Baier | 436/180 |
| 6,269,846 B1 | 8/2001 | Overbeck et al. | 141/1 |

(Continued)

OTHER PUBLICATIONS

Blanchard, A.P. et al. "High-density oligonucleotide arrays" *Biosensors & Bioelectronics* 11(6/7):687-690 (1996).

(Continued)

*Primary Examiner*—Jill Warden
*Assistant Examiner*—Brian R Gordon
(74) *Attorney, Agent, or Firm*—Lahive & Cockfield, LLP; Anthony A. Laurentano

(57) ABSTRACT

A two-pin liquid sample dispensing system is provided. The two-pin dispensing system comprises a pair of separately movable pins for holding a droplet of liquid therebetween. Each pin includes a tip spaced predetermined distance from the other pin to define a sample acquisition region. The pins acquire and hold a droplet of the liquid sample in the sample acquisition region formed in the space between the tips and apply the droplet to a selected sample handing system. The distance between the tips is variable to accommodate different liquid samples having varying physical properties and to vary the volume of the acquired droplet.

40 Claims, 7 Drawing Sheets

U.S. PATENT DOCUMENTS

| | | | | |
|---|---|---|---|---|
| 6,296,702 | B1 | 10/2001 | Bryning et al. | 118/401 |
| 6,303,387 | B1 | 10/2001 | Birch et al. | 436/180 |
| 6,309,891 | B1 | 10/2001 | Shalon et al. | 436/180 |
| 6,365,349 | B1 | 4/2002 | Moynihan et al. | 435/6 |
| 6,387,330 | B1 | 5/2002 | Bova et al. | 422/100 |
| 6,413,586 | B1 | 7/2002 | Vann et al. | 427/256 |
| 6,455,352 | B1 * | 9/2002 | Pikarsky et al. | 438/109 |
| 6,565,813 | B1 * | 5/2003 | Garyantes | 422/102 |
| 2001/0005545 | A1 | 6/2001 | Andou et al. | 428/209 |
| 2001/0049149 | A1 | 12/2001 | Kennedy et al. | 436/180 |

OTHER PUBLICATIONS

Lemieux, B. et al. "Overview of DNA chip technology" *Molecular Breeding* 4:277-289 (1998).

Schena, M. et al. "Microarrays: biotechnology's discovery platform for functional genomics" *Trends in Biotechnology* 16(7):301-306 (Jul. 1998).

Shalon, D. et al. "A DNA Microarray System for Analyzing Complex DNA Samples Using Two-color Fluorescent Probe Hybridization" *Genome Research* 6(7):639-645 (Jul. 1996).

* cited by examiner

MICROFABRICATED TWO-PIN LIQUID SAMPLE DISPENSING SYSTEM

REFERENCE TO RELATED APPLICATIONS

This application claims priority to U.S. Provisional Patent Application No. 60/325,001 filed Sep. 25, 2001 and is related to application Ser. No. 10/028,852, filed on Dec. 21, 2001, entitled "Microfluidic System Including a Virtual Wall Fluid Interface Port for Interfacing Fluids with the Microfluidic System", filed herewith; application Ser. No. 10/027,484, filed on Dec. 21, 2001, entitled "Microfluidic System Including a Virtual Wall Fluid Interface Port for Interfacing Fluids with the Microfluidic System", filed herewith; application Ser. No. 10/027,516, filed on Dec. 21, 2001, entitled "Microfluidic System Including a Virtual Wall Fluid Interface Port for Interfacing Fluids with the Microfluidic System", filed herewith; application Ser. No. 10/027,922, filed on Dec. 21, 2001, entitled "Droplet Dispensing System", filed herewith. The contents of the foregoing patent applications are herein incorporated by reference. The contents of all references, issued patents, or published patent applications cited herein are expressly incorporated by reference.

FIELD OF THE INVENTION

The present invention relates to a liquid dispensing system for forming and dispensing droplets of a liquid sample.

BACKGROUND OF THE INVENTION

Many chemical, biomedical, bioscience and pharmaceutical industries require chemical operations, such as reactions, separations and subsequent detection steps, to be performed on samples. It is generally desirable to introduce these samples into a sample handling system, such as a microfluidic system capable of handling and analyzing chemical and biological specimens, quickly, efficiently and in a highly controllable manner.

Many methods have been described for the interfacing of fluids, e.g., samples, analytes, reagents, precursors for synthesis and buffers, towards, within or between microfluidic systems. Generally, introduction of a liquid sample to a microfluidic system is accomplished through sample channels or sample wells. To introduce a liquid sample to the microfluidic system, a capillary tube may be provided, which dispenses a liquid sample to a sample well, sample channel or other sample introduction port. A significant drawback of using a capillary tube concerns the low injection efficiency inherent to capillary tubes, that is, the ratio between the volume of liquid required for a particular chemical operation in a part of the microfluidic system, and the total volume of liquid required for the introductory operation. Moreover, it is generally difficult to control the precise volume of dispensed sample using capillary tubes. Furthermore, capillary tubes are subject to contamination, because the same port used to fill the tube is also used to eject the liquid sample.

U.S. Pat. No. 6,101,946 of Martinsky, the contents of which are herein incorporated by reference, describes a pin-based system for printing microarrays of biochemical substances. The microarray printing system comprises a stainless steel printing pin having a sample channel and a flat tip that is machined with an electronic discharge machine (EDM). The pin applies a biochemical substance by filling the sample channel and subsequently directly contacting a printing substrate, to deliver the sample from the sample channel to the printing substrate. A drawback of the pin-based system described in the '946 patent concerns the ability to control the amount of delivered sample. The pin-based system is subject to contamination and breakage, because it requires direct contact between the pin tip and the printing substrate. Another drawback concerns the difficulty of precisely positioning the tip of the pin to provide sufficient contact to result in delivery of a sample.

U.S. Pat. No. 6,110,426 of Shalon et al., the contents of which are herein incorporated by reference, describes a capillary dispenser for forming microarrays of biological samples. The capillary dispenser comprises an elongate open capillary channel adapted to hold a liquid sample. The channel is formed by a pair of spaced-apart, coextensive, elongate members, which are tapered toward one another and converge at a tip region at the lower end of the channel. The elongate members are fixed relative to each other and the capillary channel is limited to a fixed volume. Furthermore, it is difficult to control the amount of sample that is acquired and dispensed from the capillary dispenser of the '246 patent.

SUMMARY OF THE INVENTION

The present invention provides a sample dispensing system comprising two microfabricated interacting pins for forming and dispensing droplets of a liquid sample. Each pin includes a tip spaced predetermined distance from the other pin to define a sample acquisition region. The pins acquire and hold a droplet of the liquid sample in the sample acquisition region formed in the space between the tips and apply the droplet to a selected sample handing system. The distance between the tips is variable to accommodate different liquid samples having varying physical properties and to vary the volume of the acquired droplet.

According to a first aspect, a droplet dispensing system is provided. The droplet dispensing system comprises two separately movable pins for holding a droplet of a liquid sample. The droplet dispensing system comprises a holder, a first pin connected to the holder and having a first tip and a second pin connected to the holder and having a second tip spaced an initial separation distance from the first tip to form a sample acquisition region for holding a predetermined volume of liquid sample. The initial separation distance is variable.

According to a second aspect, a method of applying a droplet of liquid sample to a substrate is provided. The method comprises providing a dispensing system comprising two pins separated by a variable distance, immersing the pin tips in a reservoir to acquire a droplet of a liquid sample, and contacting the substrate to deposit a spot of the liquid sample on the substrate. The spot has a predetermined volume less than the volume of the droplet.

According to another aspect, a method of diluting a first liquid sample in a second liquid is provided. The method comprises providing a dispensing system comprising two pins having a first tip and a second tip separated from the first tip by a variable distance, acquiring a droplet of the first liquid sample between the pins and immersing the pin tips containing the droplet of the first liquid sample in a second reservoir containing a second liquid, whereby the droplet of the first liquid sample is diffused into the second liquid.

According to another aspect, a two-pin droplet dispensing system is provided. The two-pin droplet dispensing system comprises a holder, a first pin connected to the holder and having a first tip and a second pin connected to the holder and having a movable tip spaced a predetermined distance from the first tip to form a sample acquisition region for holding a predetermined volume of liquid sample. The system further comprises a driver for effecting movement of the movable tip with respect to the first tip.

According to a final aspect, a liquid sample dispensing system comprising a holder a first pin having a first tip and a relaxation region for absorbing an impact on the tip is provided.

DETAILED DESCRIPTION OF THE ILLUSTRATIVE EMBODIMENTS

The present invention provides a dispensing system for dispensing a predetermined volume of liquid sample. The dispensing system of the present invention provides precise acquisition and delivery of a liquid sample to a sample handling system using two interacting pins. The dispensing system is suitable for use in a basic research or a commercial environment. The dispensing system significantly improves sample introduction into a sample handling system by increasing the efficiency, speed and controllability of forming and dispensing droplets while significantly reducing waste and contamination. The invention will be described below relative to an illustrative embodiment. Those skilled in the art will appreciate that the present invention may be implemented in a number of different applications and embodiments and is not specifically limited in its application to the particular embodiment depicted herein.

Figure 1A:
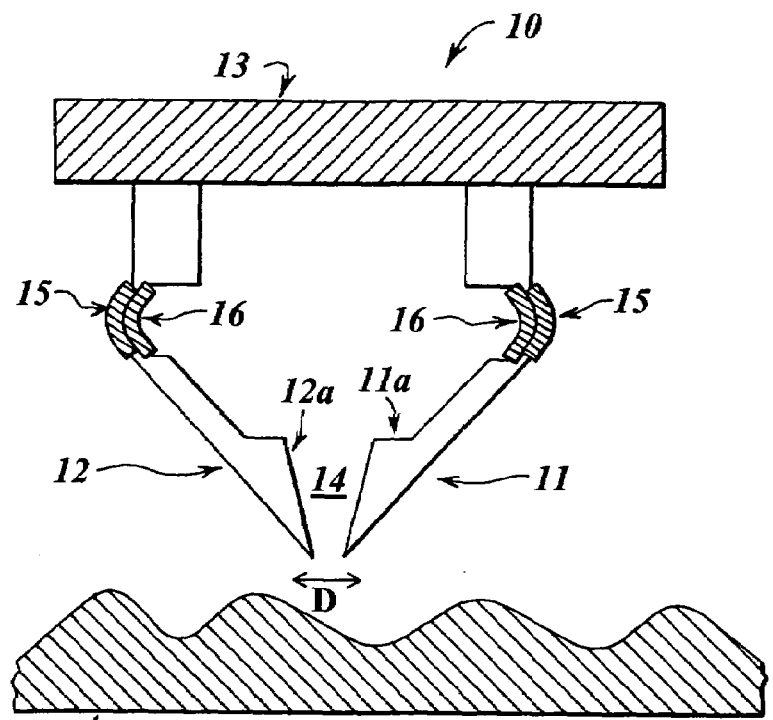
FIGS. 1a and 1b illustrate the two-pin dispensing system of an illustrative embodiment in a sample acquisition mode.
Figure 1B:
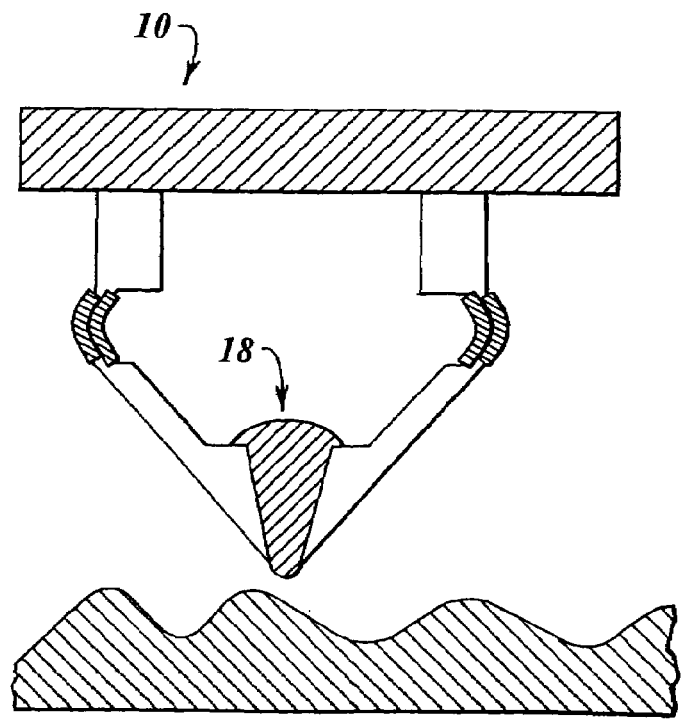

FIGS. 1a and 1b illustrate a two-pin dispensing system 10 of an illustrative embodiment of the present invention in a sample acquisition mode for acquiring a droplet of a liquid sample having a predetermined volume from a reservoir containing a supply of the liquid sample. The illustrative two-pin dispensing system 10 comprises a pair of separately movable, interacting pins sized and configured to hold a droplet of liquid between the tips of the pins. The two-pin dispensing system 10 comprises a first pin 11 and a second pin 12, which are movably connected to a holder 13. The tips 11a, 12a are separated by an initial separation distance D to form a sample acquisition region 14 in the space between the tips. The position of each pin is controlled using actuators 15 located in one or more of the pins 11, 12. According to an alternate embodiment, sensors 16 are provided on one or more of the pins 11, 12 to measure the separation distance D between the pin tips 11a, 12a. Those of ordinary skill in the art will readily recognize that the holder of the invention can include any suitable structure for retaining or holding the pins.

To acquire a droplet of a liquid sample, such as a biological sample, the pin tips 11a, 12a are immersed in a reservoir 17 containing a supply of a selected liquid sample. The pin tips 11a, 12a are positioned to allow capillary flow into to sample acquisition region 14. The capillary force induced in the sample acquisition region 14 pulls a droplet 18, having a volume defined by the separation distance of the pin tips 11a, 11b, into the sample acquisition region 14. The capillary force produced between the surfaces of the pin tips holds the droplet in the sample acquisition region 14 formed between the two pin tips 11a, 11b. The actuators 15 in the pins 11, 12 move the pins to vary the separation distance D between the tips, thereby varying the amount of sample that is acquired by the two-pin dispensing system, or to dispense the sample therefrom.

According to the illustrative embodiment, the two-pin dispensing system 10 is configured to acquire liquid samples in volumes between about fifty picoliters and about fifty nanoliters. One skilled in the art will recognize that the acquired volume is not limited to this range and that the pins may be spaced apart to accommodate any suitable volume of liquid.

The actuators 15 can also compensate for varying physical properties of the particular liquid sample, such as viscosity, surface tension, and the like, by modifying the separation distance D between the pins. The sensors 16 may also be utilized to measure the force applied between the tips and the physical properties of the acquired liquid sample on the fly. In this manner, the settings (i.e. the pin separation distance) of the pin dispensing system 10 can be modified to compensate for variations in the measured properties of the liquid sample in real time.

According to the illustrative embodiment, the droplet dispensing system 10 is fabricated from a silicon wafer using a microfabrication technique, such as a standard photolithography etching process, to fabricate the pin structures. One skilled in the art will recognize that alternative materials and manufacturing techniques may be utilized. For example, the pin dispensing system may be made out of glass, plastic or any other suitable material. According to one embodiment, an array of droplet dispensing systems 10, each comprising two pins having a variable separation distance, may be formed on a single substrate, such as a silicon wafer. For example, an array of up to about 300 or more two-pin dispensing systems 10 may be formed on a four-inch silicon wafer.

Figure 2:
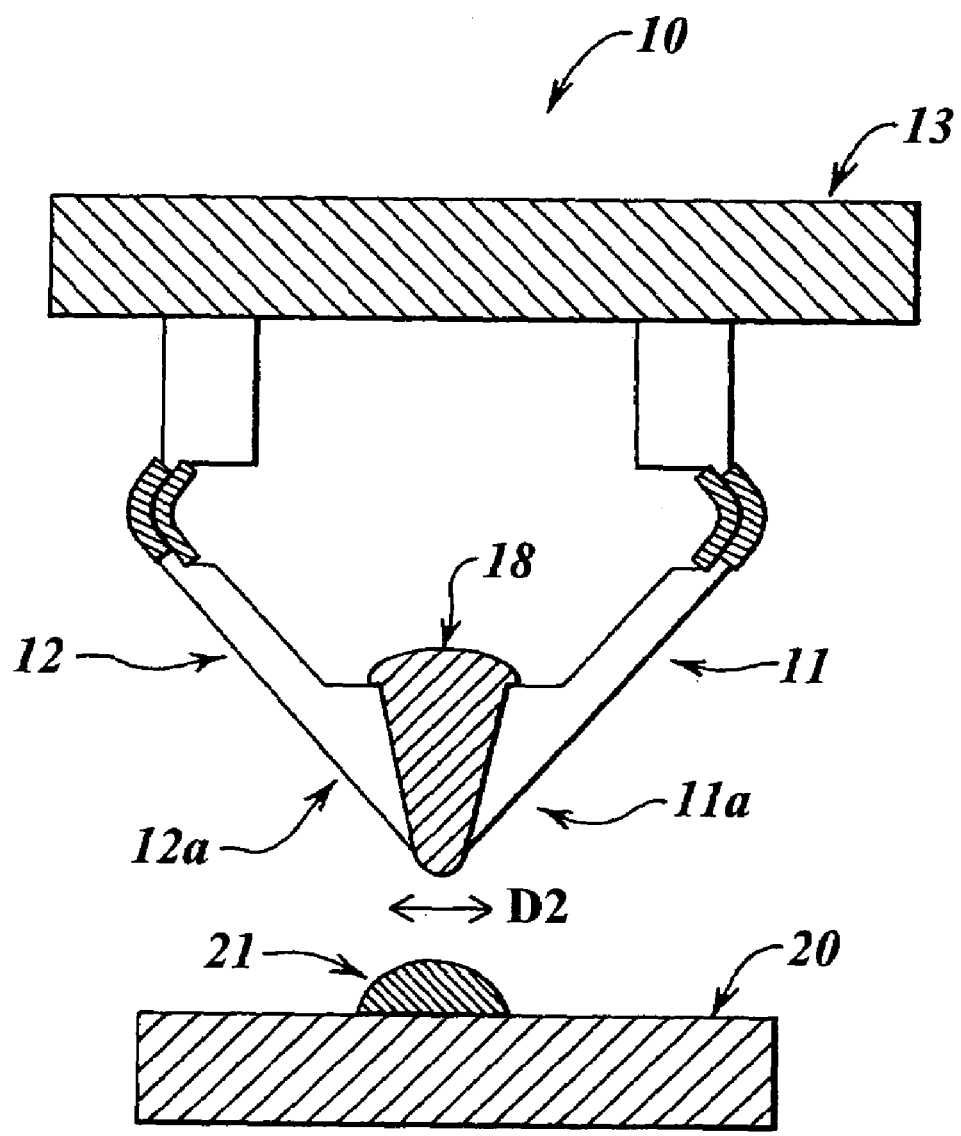
FIG. 2 illustrates the two-pin dispensing system of an illustrative embodiment in a spotting mode.

FIG. 2 illustrates the two-pin dispensing system 10 of the illustrative embodiment in a spotting mode. The two-pin dispensing system 10 may be utilized as a spotting system for printing or discharging arrays of biochemicals, such as nucleic acid molecules or proteins, or other suitable liquid samples to a sample handing system, such as a printing substrate, titre plate, microfluidic system or device, and the like for use in proteomics, genomics, screening, diagnostics and other applications. After the dispensing system acquires a droplet, the dispensing system is moved in close proximity to a surface 20. The surface 20 may comprise a solid surface or a liquid. The surface 20 may comprise a porous structure, such as a porous membrane, or a non-porous structure, such as a microscope slide. The loaded pins deposit a spot 21 on the surface 20 having a selected spot volume by direct contact between the pin tips 11a, 11b and the surface. The separation distance D2 during contact may be varied to increase or decrease the volume of the dispensed spot of the liquid sample. According to the illustrative embodiment, the volume of the dispensed spot 21 is significantly smaller than the volume of the acquired droplet 18, and is generally sub-nanoliter in volume, though one skilled in the art will recognize that the invention is not limited to this range.

The use of the two-pin dispensing system of the illustrative embodiment in spotting applications provided enhanced control over the size of the deposited spots in a microarray, and also allows for smaller spots to be formed and deposited.

Figure 3A:
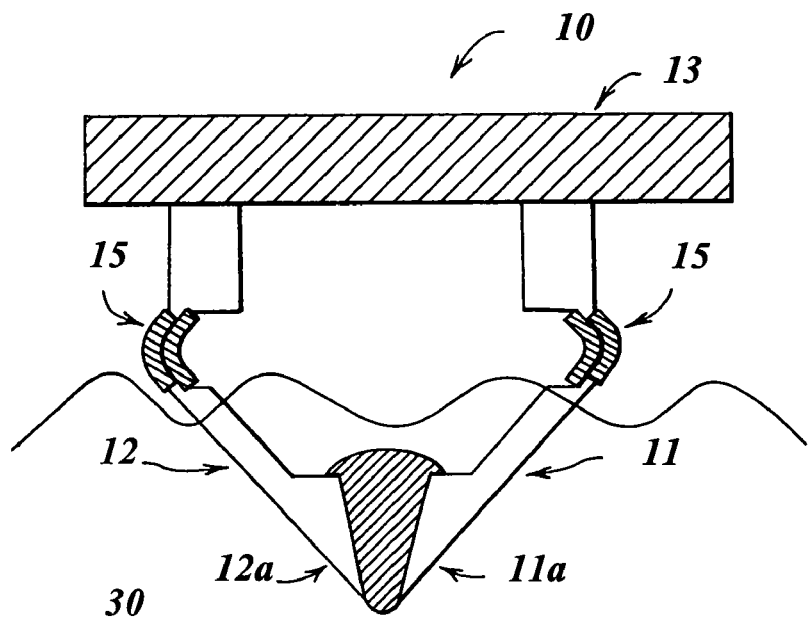
FIGS. 3a and 3b illustrate the two-pin dispensing system of an illustrative embodiment in a dilution mode.
Figure 3B:
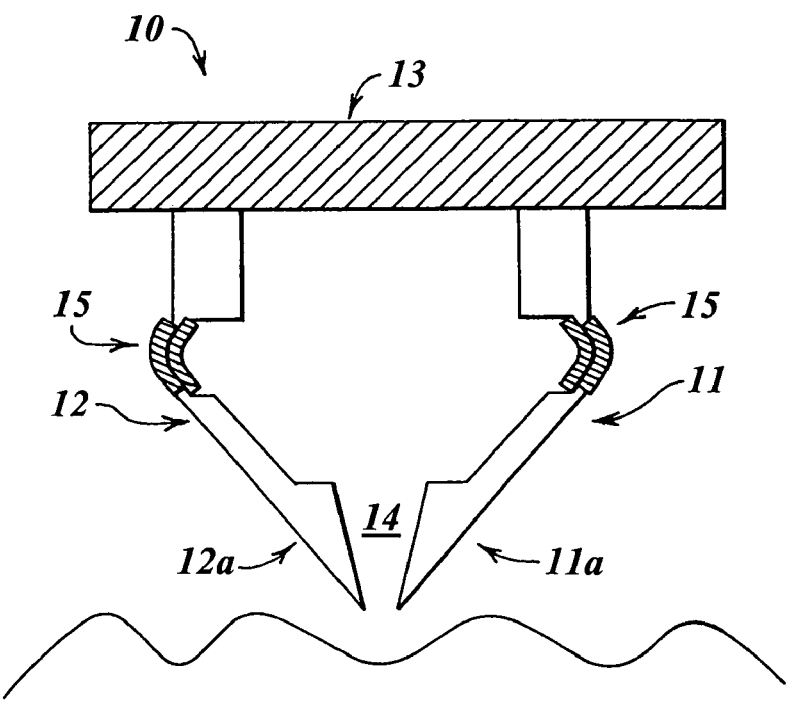

The pin dispensing system may further be utilized as a wet deposit system with dilution to dilute a selected volume of a first liquid in a second liquid sample. FIGS. 3a and 3b illustrate the two-pin dispensing system 10 in a dilution mode, wherein the acquired droplet 18 of a sample is diluted in a larger supply of a target fluid 30. After the dispensing system 10 acquires a droplet 18, the size of which is defined by the separation distance of the pin tips 11a, 12a, the pin tips 11a, 12a are immersed in a reservoir 30 containing a target fluid. The droplet 18 automatically dilutes into the target fluid via mixing and diffusion. To accelerate the dilution process, the separation distance of the tips 11a, 12a may be increased during dilution using the actuators 15.

Figure 4:
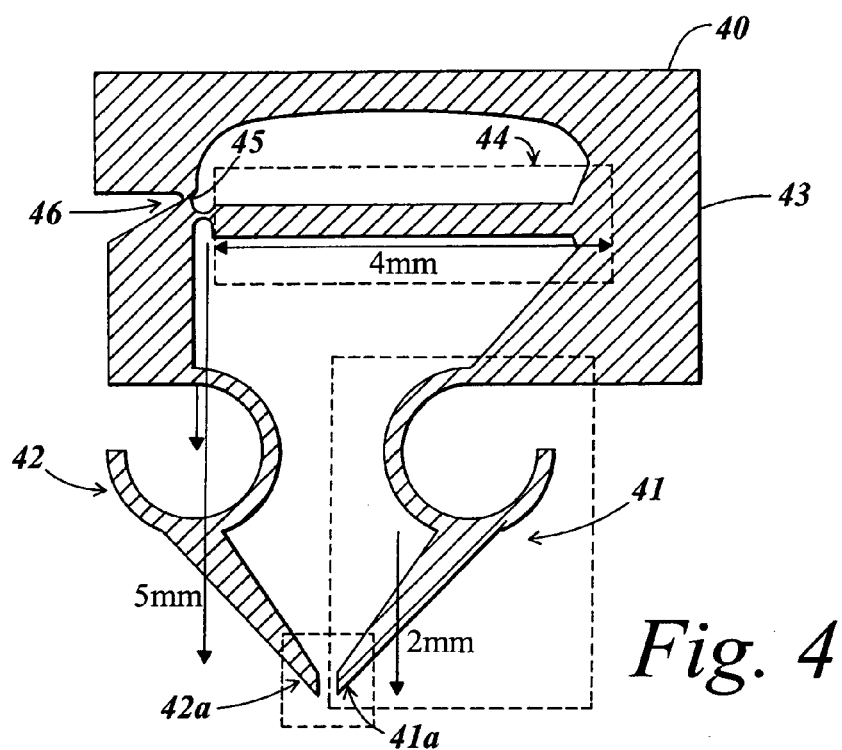
FIG. 4 illustrates an alternative embodiment of the two-pin dispensing system, including a fixed pin and a movable pin.

FIG. 4 illustrates a two-pin dispensing system 40 having a fixed pin and a movable pin according to an alternate embodiment of the invention. In the two-pin dispensing system of FIG. 4, the resting position of a first pin 41 is fixed relative to a substrate 43 and the resting position of the second pin 42 is movable relative to the first pin 41 and the substrate 43. The two-pin dispensing system 40 further includes a driver 44 for varying the separation distance between the tips 41a, 42a by adjusting the position of the second movable pin 42 in a fulcrum region 46. According to the illustrative embodiment, the movable pin rotates about a fixed pivot point 45 under the control of the driver 44 to adjust the separation distance at the tips. According to the illustrative embodiment, the pins 41, 42 further include a relaxation region 51 for preventing breakage of the tips. One skilled in the art will recognize that the relaxation region 51 may be formed in one or both of the pins 41, 42 of the two-pin dispensing system 40.

The illustrative two-pin dispensing system 40 is formed from a silicon wafer using a standard photolithography etching process to fabricate the pins 41, 42, the relaxation region 51, the driver 44, and the fixed point 45 of the fulcrum region 46 in the wafer substrate 43. According to the illustrative embodiment, the two-pin dispensing system 40 is fabricated from a silicon wafer having dimensions of about one square centimeter. The pins 41, 42 have a length of about five millimeters, though one skilled in the art will recognize that the invention is not limited to this size. According to an alternate embodiment, a larger silicon wafer or other suitable substrate is provided, and an array of pin dispensing systems is fabricated on the larger silicon wafer. For example, a silicon wafer having a size of about ten square centimeters may be used to fabricate an array of about seventy two-pin dispensing systems 40 thereon. A fifteen square centimeter silicon wafer can be utilized to fabricate over one hundred two-pin dispensing systems 40 in the silicon wafer substrate.

Those of ordinary skill will readily recognize that any suitable configuration can be employed to move one or both of the pins.

Figure 5:
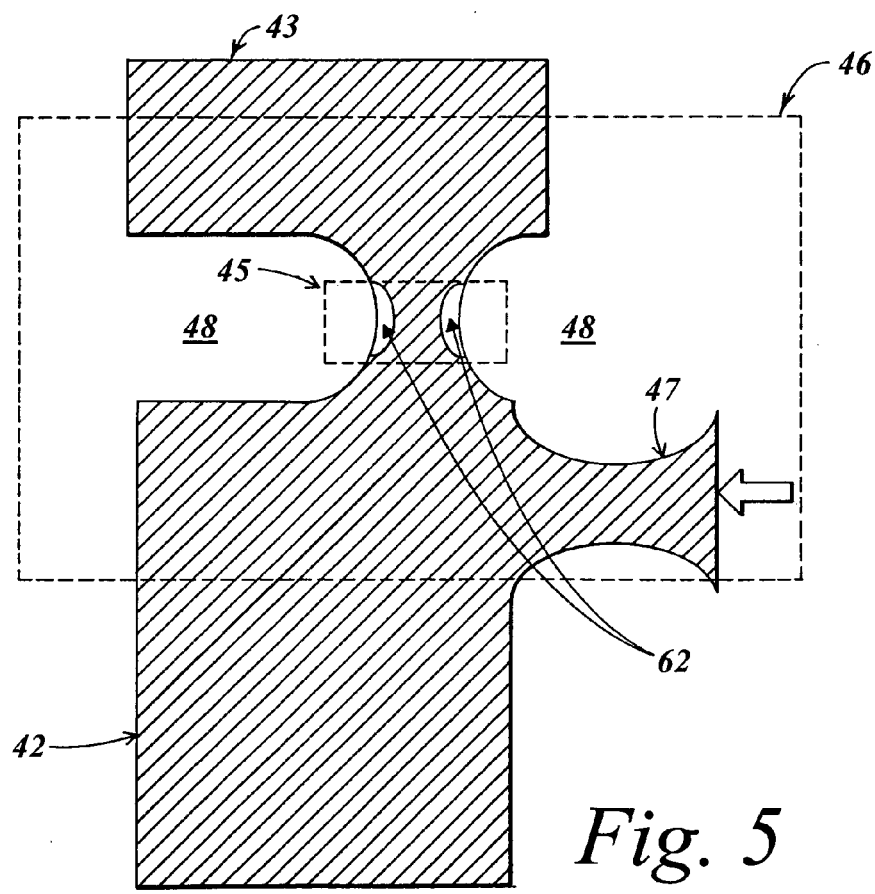
FIG. 5 is a detailed view of the fulcrum region of the two-pin dispensing system of FIG. 4.

FIG. 5 is a detailed view of the fulcrum region 46 of the two-pin dispensing system of FIG. 4. The movable pin 42 is configured to pivot about a fixed point 45 to vary the separation distance of the two pin tips. The driver 44 applies a force to an application region 47 of the fulcrum region 46 to cause the movable pin 42 to rotate, thereby effecting movement of the movable pin tip 42a relative to the tip 41a of the fixed pin 41. As illustrated, the fulcrum region 46 includes gaps 48 are formed in the substrate 43 adjacent to the fixed point 45 to allow for rotation of the pin 42 about the fixed point in response to activation of the driver 44.

According to an alternate embodiment of the invention, the fulcrum region further includes bending sensors, illustrated as piezoresistors 62, on the left and right side of the fulcrum region to allow differential sensing of actual bending of the pin 42 in the fulcrum region. In this manner, the amount of bending, and the resultant tip separation distance may be controlled using a closed loop feedback system. The use of bending sensors further limits nonlinear temperature effects by allowing real-time sensing of tip displacement.

Figure 6:
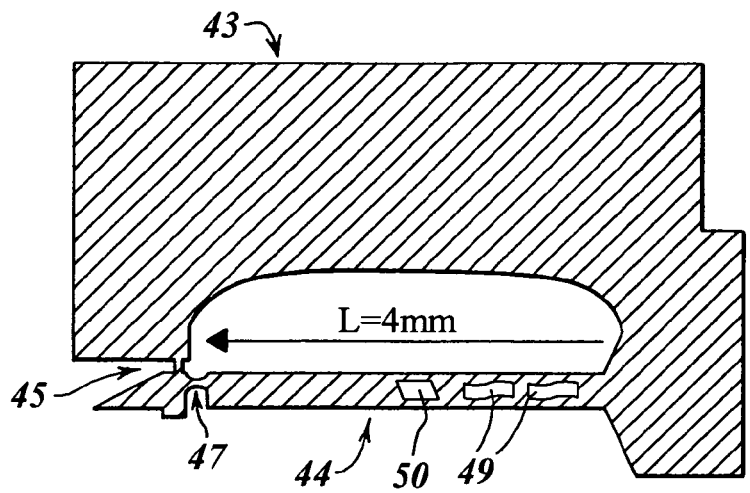
FIG. 6 is a detailed view of the driver of the two-pin dispensing system of FIG. 4.

FIG. 6 is a detailed view of the driver 44 of the two-pin dispensing system 40 of FIG. 4. As shown the driver 44 comprises a bar of silicon that imparts a force on the application region 47 of the fulcrum 46 to move of tip 42a a predetermined amount. According to the illustrative embodiment, the driver 44 expands a predetermined amount in response to a temperature increase. The expansion of the driver 44 forces rotation of the fulcrum about the pivot point. According to the illustrative embodiment, the system is configured such that the ratio between the amount of movement of the tip 42a in response to expansion of the driver 44 to the amount of expansion of the driver is greater than one hundred. In other words, a driver expansion of one micron causes a one hundred micron displacement of the pin tip 42a.

According to the illustrative embodiment, the driver 44 has an initial length L of four millimeters. A thirty-degree rise in temperature of the silicon results in a 1.08 micrometer expansion of the driver 44. The expansion of the driver 44 forces the pin 42 to rotate about the fixed pivot point 45, thereby increasing the separation distance between the tips 41a, 42a by greater than 108 microns.

According to the illustrative embodiment, heating resistors 49 are affixed to the driver for applying heat to the driver 44. The heating resistors may comprise poly resistors, diffused resistors or any suitable means for applying heat to the driver 44 in order to effect controlled expansion of the driver 44 and to vary the separation distance between the tips 41a, 42a. Optionally, cooling fins (not shown) are provided in the driver 44 near the fulcrum region 45 to prevent unwanted heating of the driver in the fulcrum region. According to an alternate embodiment, a temperature sensor 50 in communication with the heating means is included in the two-pin dispensing system 40 to provide closed loop control of the driver 44 temperature.

One skilled in the art will recognize that the two-pin dispensing system is not limited to the illustrative driver. According to alternate embodiments the driver 44 comprises an electrostatic system, a piezoelectric system, an electromechanical system, a thermoelectric actuator or any suitable system for applying a predetermined and defined force to cause controlled adjustment of the separation distance between the pin tips 41a, 42a. One skilled in the art will further recognize that the two-pin dispensing system is not limited to a fulcrum for varying the separation distance and that any suitable mechanism for varying the separation distance may be utilized.

Figure 7A:
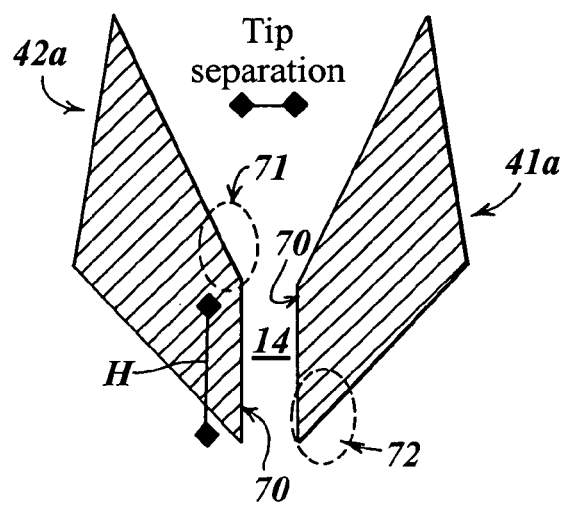
FIGS. 7a, 7b and 7c are detailed views of the tip region of the two pins of the pin dispensing system of FIG. 4.
Figure 7B:
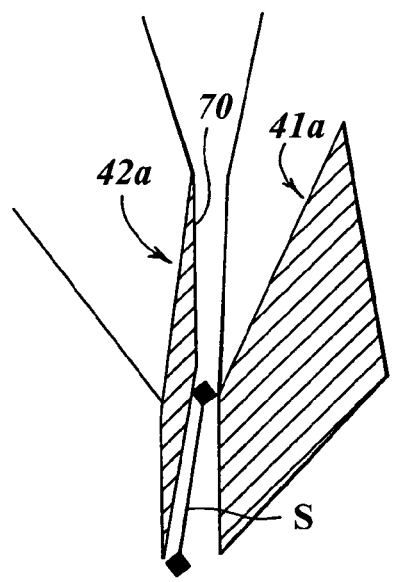

FIGS. 7a and 7b are detailed views of the tip region of the two pins of the two-pin dispensing system 40 of FIG. 4. As discussed, the tips 41a, 42a are spaced apart a predetermined distance D, which is defined by the driver 44. Each tip includes a sample contact surface 70, defined by the tip height H and the tip depth S, which are fixed values determined by the shape of the sample surfaces 70. The volume of the sample acquisition region 14 and thus the volume of an acquired sample droplet corresponds to the volume of the space defined between the tips, or the product of the tip height H, the tip depth S and the separation distance D. For example, according to the illustrative embodiment, the separation distance D between the pin tips 41a, 42a is between about twenty-five microns and about one hundred twenty five microns. For tips having a tip depth of about fifty microns and a height of about two hundred microns, the resulting volume of a captured droplet is between about 250 picoliters and about 1.25 nanoliters. For tips having a tip depth of 100 microns and a height of about 400 microns, a tip separation distance between about 25 and 125 microns results in an acquired droplet having a volume of between about 1.0 nanoliters and about 5 nanoliters. Tips having a depth of 500 microns and a height of 500 microns, form a droplet having a volume between about 6.25 nanoliters and about 31.5 nanoliters when the separation distance between the tips is between about 25 and about 125 microns.

The tip contact surfaces 70 defined by the tip heights H and tip depths S may form parallel faces or, according to a preferred embodiment, may be tapered, so that the separation distance D is reduced towards the bottom and/or front of the tip surface. In this manner, smaller droplet volumes may be accommodated. The slope of the tips 41a, 42a may be varied in regions 71 and 72 to improve droplet shape and enhance delivery of the droplet.

Figure 7C:
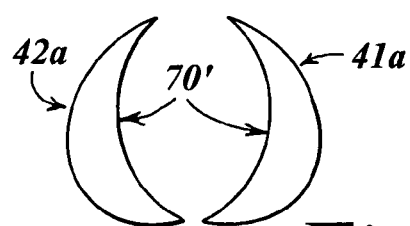

FIG. 7c is a cross-sectional view of the tips 41a, 42a according to an alternate embodiment. According to the alternate embodiment, the tip surfaces 70' are curved to hold form a cylindrical or conical sample acquisition region 14 therebetween.

According to alternate embodiment, the one or both of the tip surfaces 70 and/or the outside shaft surface are coated with a hydrophilic, hydrophobic or other chemical coating to enhance droplet acquisition and dispensing. For example, the tips 41, 42 may be formed of or coated with a hydrophilic coating to enhance retention of a sample in the sample acquisition region. According to one embodiment, the outside shaft surfaces of the tips 41,42 are coated with gold or another suitable hydrophobic material without affecting the tip surfaces 70 defining the sample acquisition region 14. The use of a metal coating provides enhanced control over the volume and release of a droplet. The use of silicon and/or gold additionally allows for more vigorous cleaning solutions to be utilized when cleaning the tips without degrading the system. In this manner, contamination of the tips is reduced.

The coating may be applied in a pattern to the tip surfaces 70 or the other surfaces of the tips 41, 42 by shadow masking. The coating may be sputtered, or evaporated on a surface in a predetermined pattern, defined by a mask. One skilled in the art will recognize that any suitable pattern for directing the liquid sample and enhancing control over sample acquisition and dispensing may be utilized.

According to another embodiment, the dispensing system may comprise a single pin having a suitable pattern coating applied to the surfaces of the pin tip. For example, the shaft of the single pin may be coated with a suitable hydrophobic coating and the tip of the pin may be coated with a suitable hydrophilic coating to enhance acquisition and dispensing of a liquid sample.

Figure 8:
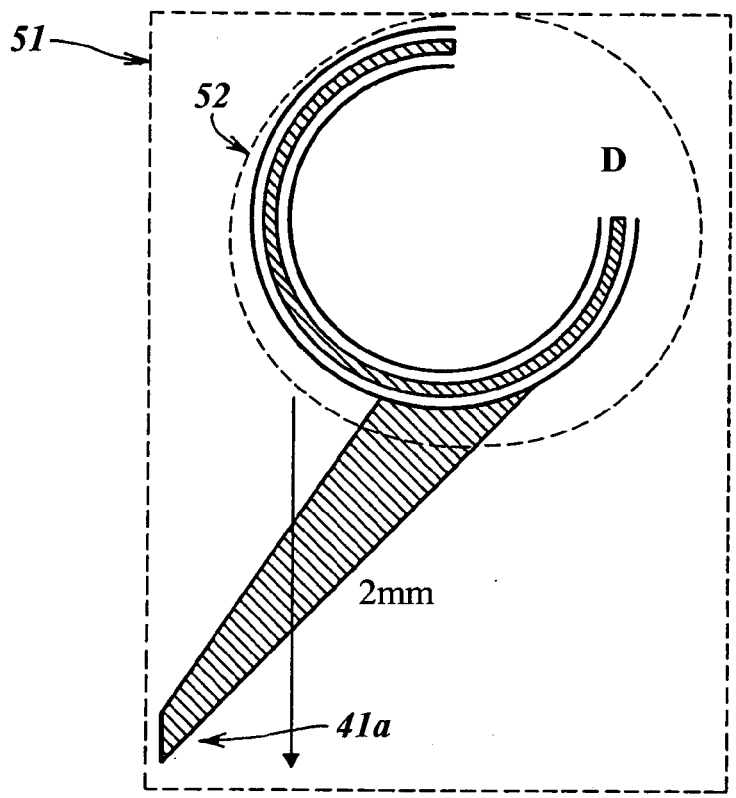
FIG. 8 illustrates the relaxation region of the pin dispensing system of FIG. 4.

FIG. 8 illustrates the relaxation region 51 of the pin dispensing system 40 of FIG. 4. The pin tips 41, 42 are brittle and subject to breakage when accidentally touched down to surfaces, due to their size and the material used to fabricate the pins. The illustrative relaxation region 51 comprises a spring 52 formed between the tip 41a and the substrate 43. When the tip 41a contacts a surface, the spring absorbs the impulse and retracts the tip 41a to prevent breakage. The springs 52 in the pins are configured to move the corresponding tip up and away from the other tip to prevent collision of the tips. The invention is not limited to the illustrative spring design. One skilled in the art will recognize that any suitable spring design may be utilized to form the relaxation region 51 to protect the pin tips from breakage.

According to an alternate embodiment, the spring 52 includes sensors to measure of the force of contact between the tip and a surface. For example, differential piezoresistive sensors may be included in the spring 52 and connected to an actuator (not shown) to control the spring using feedback control loop. The spring sensor may also be utilized to measure the force exerted by the droplet on the tips, and allow the driver to compensate for variable forces exerted by the droplet on the tips.

According to an alternate embodiment of the present invention, a relaxation region may be implemented in a two-pin dispensing system comprising a pair of spaced-apart, fixed pins defining a sample acquisition region of fixed volume.

As discussed, the two-pin dispensing system 10 or 40 of the illustrative embodiment may be microfabricated from a suitable substrate, such as silicon, glass or plastic. According to the illustrative embodiment, photolithography may be utilized to form the pin structures in the substrate. In photolithography, the pattern of the two pins and other components of the two-pin dispensing system 10 or 40 are imprinted on a silicon wafer, or other substrate, using one or more photoresist layers that are patterned by UV or other light projected through one or more photo-masks containing the pattern on it. The substrate is then etched to fabricate the two-pin structure. One skilled in the art will recognize that any suitable microfabrication technique may be utilized to manufacture the two-pin dispensing system of the illustrative embodiment of the present invention.

One skilled in the art will recognize that the described microfabrication technique may further be utilized to fabricate single-pin dispensing systems from a silicon wafer or other suitable substrate. For example, it is within the scope of the invention to microfabricate a single-pin structure having two tips forming a sample channel for acquiring and dispensing a liquid sample, as described in U.S. Pat. No. 6,101,946, from a silicon wafer by etching the silicon wafer to define the pin and sample channel.

Figure 9:
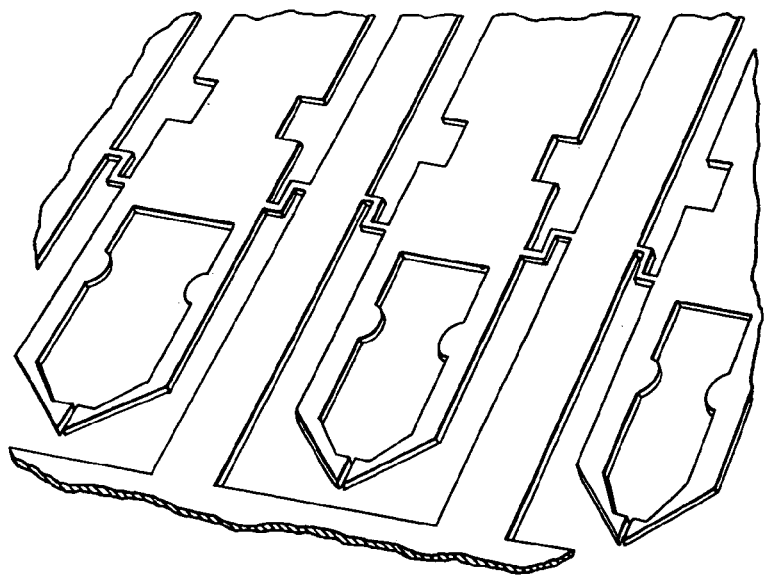
FIG. 9 is a scanning electron microscope (SEM) image of an array of two-pin dispensing systems that are microfabricated from a silicon wafer according to the teachings of the illustrative embodiment of the present invention.

FIG. 9 is a scanning electron microscope (SEM) image of an array of two-pin sample dispensing systems 100 according to an embodiment of the invention and formed from a silicon wafer 101 using the above-described microfabrication technique. As shown, a plurality of two-pin dispensing systems are fabricated from a single silicon wafer substrate. Each two-pin dispensing system comprises a pair of elongated pins that are spaced apart to define a sample acquisition region between the tips of the pins.

Figure 10:
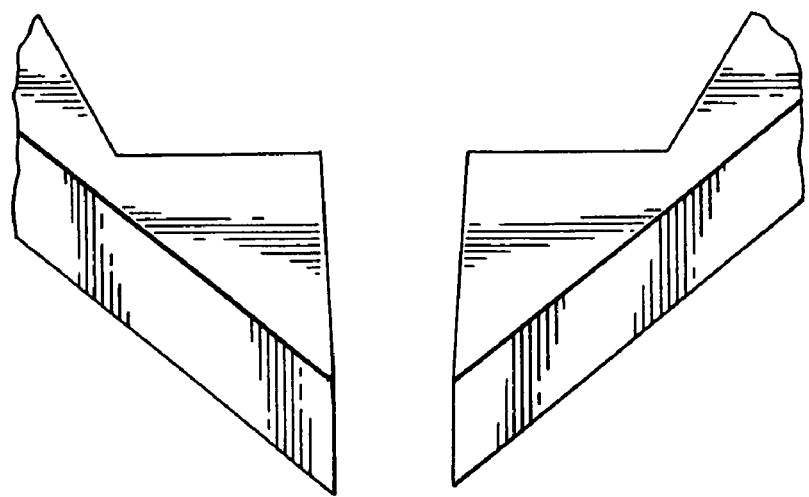
FIG. 10 is a SEM image showing a detailed view of a tip region of one of the two-pin dispensing systems of FIG. 9.

FIG. 10 is another SEM image showing a detailed view of the tip region of one of the microfabricated two-pin dispensing systems of FIG. 9. As shown, the pins are etched in a silicon wafer to define a sample acquisition region 140 between the tips of the pins. As illustrated, the microfabricated pin tips have a separation distance of less than about 100 microns.

Figure 11:
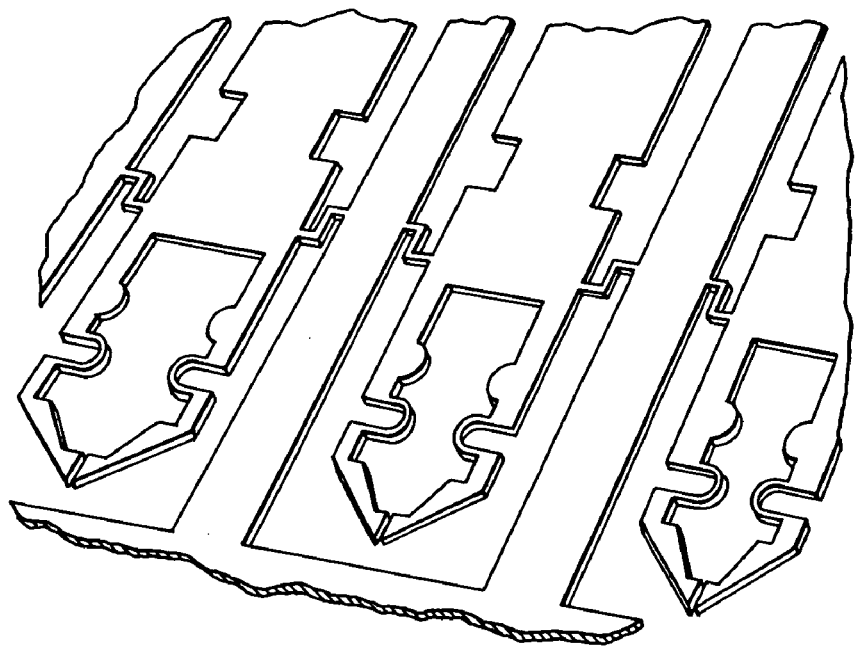
FIG. 11 is a SEM image illustrating an array of two-pin dispensing systems having relaxation regions that are microfabricated from a silicon wafer according to the teachings of the illustrative embodiment of the present invention.

FIG. 11 is another SEM image of an array of microfabricated two-pin sample dispensing systems 110 having relaxation regions 51 according to an embodiment of the invention. As shown, the array is also formed from a silicon wafer 101 using the above-described microfabrication technique. The relaxation region 51 is formed by etching the silicon wafer in the region between the pin tips and the holder to define a spring for absorbing an impact on the tips. The relaxation region 51 prevents breakage of the pin tips 41, 42 when the pin tips contact a surface.

The two-pin dispensing system provides significant improvements to the process of forming and dispensing droplets of samples for spotting and dilution applications. The illustrative configuration provides precise control over the amount of liquid sample that is acquired and deposited through the use of two pins having a variable separation distance. Adjusting the separation distance between the pin tips easily and precisely modifies the volume of the acquired liquid droplet and the deposited liquid droplet. Furthermore, measurements of the physical properties of the liquid volume can be made on the fly and the tip separation can be modified quickly and easily to compensate for variations. The use of sensors provides precise control of the tip separation distance to optimize the process of acquiring and dispensing droplets of a liquid sample.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and protected by Letters Patent is:

1. A liquid sample dispensing system, comprising: a holder; a first pin coupled to the holder and having a first tip; and a second pin coupled to the holder and having a second tip spaced a predetermined separation distance D from the first tip, wherein the first and second pins are movable relative to each other; and at least one sensor for measuring the physical properties of a liquid sample held between the first tip and the second tip; wherein said at least one sensor is provided on at least one of said first and second pins.

2. The liquid sample dispensing system of claim 1, further comprising a first actuator for moving the first tip to vary the initial separation distance.

3. The liquid sample dispensing system of claim 1, further comprising a second actuator for moving the second tip to vary the initial separation distance.

4. The liquid sample dispensing system of claim 1, wherein said at least one sensor also senses the separation distance between the first tip and the second tip.

5. The liquid sample dispensing system of claim 1, further comprising an actuator for varying the separation distance in response to the measurement of the physical properties.

6. The liquid sample dispensing system of claim 1, wherein the first pin and the second pin are fabricated from a silicon wafer.

7. The liquid sample dispensing system of claim 1, wherein the first tip and a second tip separated from the first tip by a variable separation distance.

8. The liquid sample dispensing system of claim 1, wherein a sample acquisition region for holding a predetermined volume of liquid sample is formed between the first pin and the second pin.

9. The liquid sample dispensing system of claim 1, further comprising a driver for effecting movement of the second pin with respect to the first pin to adjust the predetermined separation distance.

10. The liquid sample dispensing system of claim 9, wherein the second pin is attached to the holder at a fixed pivot point.

11. The liquid sample dispensing system of claim 10, wherein the driver rotates the second pin about the fixed pivot point to adjust the predetermined separation distance.

12. The liquid sample dispensing system of claim 10, wherein the driver applies one of a predetermined force and a predetermined displacement to the second pin to rotate the second pin a predetermined amount.

13. The liquid sample dispensing system of claim 9, wherein the driver comprises a silicon bar.

14. The liquid sample dispensing system of claim 13, wherein the silicon bar expands a predetermined distance to apply the predetermined force to the second pin.

15. The liquid sample dispensing system of claim 9, wherein the driver comprises a piezoelectric assembly for moving the second pin.

16. The liquid sample dispensing system of claim 9, wherein the driver comprises an electromechanical assembly for moving the second pin.

17. The liquid sample dispensing system of claim 9, wherein the driver comprises a thermoelectric assembly for moving the second pin.

18. The liquid sample dispensing system of claim 11, further comprising a bending sensor for detecting the rotation of the second pin about the fixed pivot point.

19. The liquid sample dispensing system of claim 18, wherein the bending sensor communicates with the driver to form a closed loop control circuit for controlling the amount of rotation of the second pin.

20. The liquid sample dispensing system of claim 13, wherein the silicon bar includes heating resistors for applying a controlled amount of heat to the silicon bar to effect expansion of the silicon bar.

21. The liquid sample dispensing system of claim 13, wherein the silicon bar includes at least one cooling fin for cooling the silicon bar.

22. The liquid sample dispensing system of claim 13, wherein the silicon bar includes a temperature sensor for detecting the temperature of the silicon bar.

23. The liquid sample dispensing system of claim 1, wherein one of the first tip and the second tip includes a chemical coating to enhance control over a liquid sample held in a sample acquisition region formed between the first tip and the second tip.

24. The liquid sample dispensing system of claim 23, wherein the chemical coating comprises a hydrophobic material.

25. The liquid sample dispensing system of claim 23, wherein the chemical coating comprises a hydrophilic material.

26. The liquid sample dispensing system of claim 23, wherein the chemical coating is applied in a predetermined pattern.

27. The liquid sample dispensing system of claim 26, wherein the predetermined pattern is determined by a mask used in applying the chemical coating to the tip.

28. The liquid sample dispensing system of claim 1, wherein the first tip includes a first contact surface and the movable tip includes a second contact surface defining a sample acquisition region for holding a predetermined volume of liquid sample.

29. The liquid sample dispensing system of claim 28, wherein the first contact surface and the second contact surface are tapered.

30. The liquid sample dispensing system of claim 28, wherein the first contact surface and the second contact surface are parallel.

31. The liquid sample dispensing system of claim 28, wherein one of said first contact surface and said second contact surface is curved.

32. The liquid sample dispensing system of claim 1, further comprising a relaxation region for absorbing an impact on at least one of the tips.

33. The liquid sample dispensing system of claim 32, wherein the relaxation region comprises a spring connecting the first tip and the holder.

34. The liquid sample dispensing system of claim 32, wherein the relaxation region comprises a spring connecting the second tip and the holder.

35. The liquid sample dispensing system of claim 32, wherein the relaxation region includes a sensor for measuring the force on the tips.

36. The liquid sample dispensing system of claim 1, wherein one of said first pin and said second pin includes a fulcrum region comprising a fixed pivot point to permit movement of the pin about the fixed pivot point.

37. The liquid sample dispensing system of claim 36, further comprising an actuator for moving the pin that includes the fulcrum region about the fixed pivot point.

38. The liquid sample dispensing system of claim 1, wherein one of said first pin and said second pin further includes a spring portion for absorbing an impact on the tip.

39. The liquid sample dispensing system of claim 1, wherein the holder, first pin and second pin are microfabricated from a substrate comprising a silicon wafer.

40. The liquid sample dispensing system of claim 1, wherein the holder, first pin and second pin are microfabricated from a substrate comprising a glass plate.

* * * * *